United States Patent [19]
Ressemann et al.

[11] Patent Number: 5,779,671
[45] Date of Patent: Jul. 14, 1998

[54] LONGITUDINALLY COLLAPSIBLE AND EXCHANGEABLE CATHETER

[75] Inventors: Thomas V. Ressemann, St. Cloud; David J. Blaeser, Champlin, both of Minn.

[73] Assignee: Scimed Life Systems, Inc., Maple Grove, Minn.

[21] Appl. No.: 787,782

[22] Filed: Jan. 23, 1997

Related U.S. Application Data

[60] Continuation of Ser. No. 516,040, Aug. 17, 1995, abandoned, which is a division of Ser. No. 220,752, Mar. 30, 1994, Pat. No. 5,466,222.

[51] Int. Cl.$^6$ ............................................. A61M 29/00
[52] U.S. Cl. .......................... 604/96; 606/192; 606/194; 604/49
[58] Field of Search .................. 604/96–103, 49, 604/51–53; 606/192–196; 600/18, 115, 116; 128/207.15

[56] References Cited

U.S. PATENT DOCUMENTS

| | | |
|---|---|---|
| 4,593,690 | 6/1986 | Sheridan et al. .................. 128/207.15 |
| 4,762,130 | 8/1988 | Fogarty et al. . |
| 5,152,277 | 10/1992 | Honda et al. . |
| 5,180,367 | 1/1993 | Kontos et al. . |
| 5,242,398 | 9/1993 | Knoll . |
| 5,246,420 | 9/1993 | Kraus et al. . |
| 5,306,261 | 4/1994 | Alliger et al. . |
| 5,334,153 | 8/1994 | McIntyre et al. .................. 604/99 |
| 5,338,301 | 8/1994 | Diaz . |
| 5,591,194 | 1/1997 | Berthiaume . |

FOREIGN PATENT DOCUMENTS

| | | |
|---|---|---|
| WO92/03095 | 3/1992 | WIPO . |
| WO93/17750 | 9/1993 | WIPO . |

*Primary Examiner*—Michael Buiz
*Assistant Examiner*—Jennifer R. Sadula
*Attorney, Agent, or Firm*—Robert E. Atkinson

[57] ABSTRACT

A balloon dilatation catheter is disclosed which incorporates a longitudinally collapsible shaft section including a longitudinally collapsible guide wire lumen. The longitudinally collapsible shaft section may also include a longitudinally collapsible inflation lumen. The longitudinally collapsible shaft section may take the form of a polymer encased braid, a polymer bellow, or a helical tube. A longitudinally rigid member may be connected to the distal end of the longitudinally collapsible shaft section in order to facilitate extension and contraction of the collapsible section. Methods of using such a catheter system are also disclosed.

6 Claims, 7 Drawing Sheets

LONGITUDINALLY COLLAPSIBLE AND EXCHANGEABLE CATHETER

This is a continuation of application Ser. No. 08/516,040, filed Aug. 17, 1995, now abandoned which is a division of application Ser. No. 08/220,752 filed on Mar. 30, 1994, now U.S. Pat. No. 5,466,222.

FIELD OF THE INVENTION

The present invention generally relates to medical devices used in combination with guide members. More specifically, the present invention relates to intravascular balloon catheters for use in combination with guide wires. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well known in the art and typically involve the use of a balloon catheter and a guide wire, possibly in combination with other intravascular devices. The balloon catheter is advanced over the guide wire such that the distal end of the balloon catheter is positioned adjacent a restriction in a diseased vessel. The balloon is inflated and the restriction in the vessel is opened.

There are two basic types of balloon catheters used in combination with a guide wire: commonly referred to as over-the-wire (OTW) catheters and rapid-exchange catheters (RX). The construction and use of both OTW catheters and RX catheters are well known in the art.

A basic OTW catheter includes an inflatable balloon mounted on one end of a long shaft and a manifold connected to the other end. The manifold has two ports: a guide wire port and an inflation port. A guide wire is slidably inserted into the guide wire port, through the shaft and out the distal end of the balloon. The guide wire extends only a short distance outside either end of the balloon catheter. In addition, when in use, only a short section of the catheter and guide wire remain outside the body. Thus, to remove the catheter while leaving the guide wire in place and retaining control of the guide wire, the length of the guide wire must be increased by attaching an extension wire. The extended guide wire allows the catheter to be removed while leaving the guide wire in place inside the body. However, this is a tedious and time consuming task which may jeopardize the patient's health when time is of the essence.

By contrast, RX catheters do not require an extension wire to remove the catheter while leaving the guide wire in place. A basic RX catheter includes an inflatable balloon mounted on one end of a long shaft and a manifold connected to the other end. The manifold only includes an inflation port, not a guide wire port. The guide wire port on a RX catheter is located on the distal end of the shaft. A guide wire is slidably inserted into the guide wire port, through only a distal portion of the shaft and out the distal end of the balloon. The guide wire is exterior to the catheter along the entire length of the catheter proximal of the guide wire port, and is interior to the catheter distal of the guide wire port. When in use, the length of the guide wire interior to the catheter is shorter than the length of the guide wire outside the body. Thus, to remove the catheter while leaving the guide wire in place, the catheter is simply slid off the wire without the need for an extension wire. The RX catheter design can save valuable time.

While RX catheters have advantages over the OTW catheters, RX catheters have a significant disadvantage. In an OTW catheter, if a guide wire requires replacement while in use, the old guide wire is removed and a new guide wire is inserted into the guide wire port on the manifold. In a RX catheter, if a guide wire requires replacement while in use, the old guide wire can be removed but the new guide wire can't be inserted because the guide wire port is located on the distal end of the shaft which is inside the body. To insert a new guide wire into a RX catheter, the RX catheter must be removed to expose the guide wire port. Removing the balloon catheter is not desirable because vascular access may be difficult to regain. Thus, while the RX catheter design is generally preferable over the OTW catheter design for quick and easy catheter exchange, the OTW catheter design is generally preferable over the RX catheter design for quick and easy guide wire exchange.

In view of the advantages of each of these features, it is desirable to have a catheter that allows for both a quick and easy catheter exchange and a quick and easy guide wire exchange.

SUMMARY OF THE INVENTION

The present invention overcomes the competing disadvantages of the prior art in a novel and non-obvious manner. One embodiment of the present invention is a balloon catheter for use in combination with a removable guide wire. The catheter includes a balloon connected to the distal end of a long shaft and a manifold connected to the other end of the shaft. The shaft defines separate guide wire and inflation lumens. A portion of the shaft is longitudinally collapsible. The collapsible section may be a polymer encased braid or a polymer bellow, but the collapsible section is not limited to such constructions.

In another embodiment of the present invention, the collapsible section defines a guide wire tube, an inflation tube and a rigid member. The features of the guide wire tube and inflation tube can be combined into a single element. Similarly, the features of the inflation tube and rigid member may be combined into a single element. The guide wire tube and the inflation tube may be formed of a polymer encased braid or a polymer bellow, but the tubes are not limited to such constructions. The rigid member may be in the form of a solid rod or a hollow tube, such as a rigid inflation tube.

In practice, the present invention is used in conjunction with a removable guide member (e.g. guide wire) and can be exchanged over the guide member. A guide wire is inserted into a patient such that the guide wire extends from a point outside the patient to a point inside the patient. Either before or after the guide wire is placed inside the patient, a balloon catheter is positioned over the guide wire such that the entire length of the balloon catheter is on the guide wire. With the balloon adjacent a restriction in a vessel, the treating physician then inflates the balloon catheter to open the restricted vessel. When the balloon catheter needs to be removed, the balloon catheter is compressed longitudinally such that the length of the balloon catheter is shorter than the length of the guide wire outside the patient. The balloon catheter can then be removed from the guide wire.

In addition to the ability to remove the catheter from the guide wire without the use of an extension wire, the present invention also has the ability to exchange a guide wire while leaving the catheter in place inside the patient. For example, in use, a guide wire is inserted into a patient such that the guide wire extends from a point outside the patient to a point inside the patient. Either before or after the guide wire is placed inside the patient, a balloon catheter is positioned over the guide wire such that the entire length of the balloon catheter is on the guide wire. If it is necessary to remove the guide wire, it is simply pulled out while the catheter retains vascular access. The treating physician then inserts a new guide wire and continues with the procedure. After the therapy is provided, the balloon catheter is compressed longitudinally such that the length of the balloon catheter is shorter than the length of the guide wire outside the patient. The balloon catheter can then be removed from the guide wire.

While the disclosure focuses on balloon catheters for intravascular use, one skilled in the art will recognize that invention may be incorporated into other devices and uses not discussed herein. Furthermore, in addition to the advantages described, other advantages of the present invention may be appreciated without departing from the spirit of the invention.

DETAILED DESCRIPTION OF THE INVENTION

The following detailed description should be read with reference to the drawings in which like elements in different figures are numbered identically.

Figure 1:
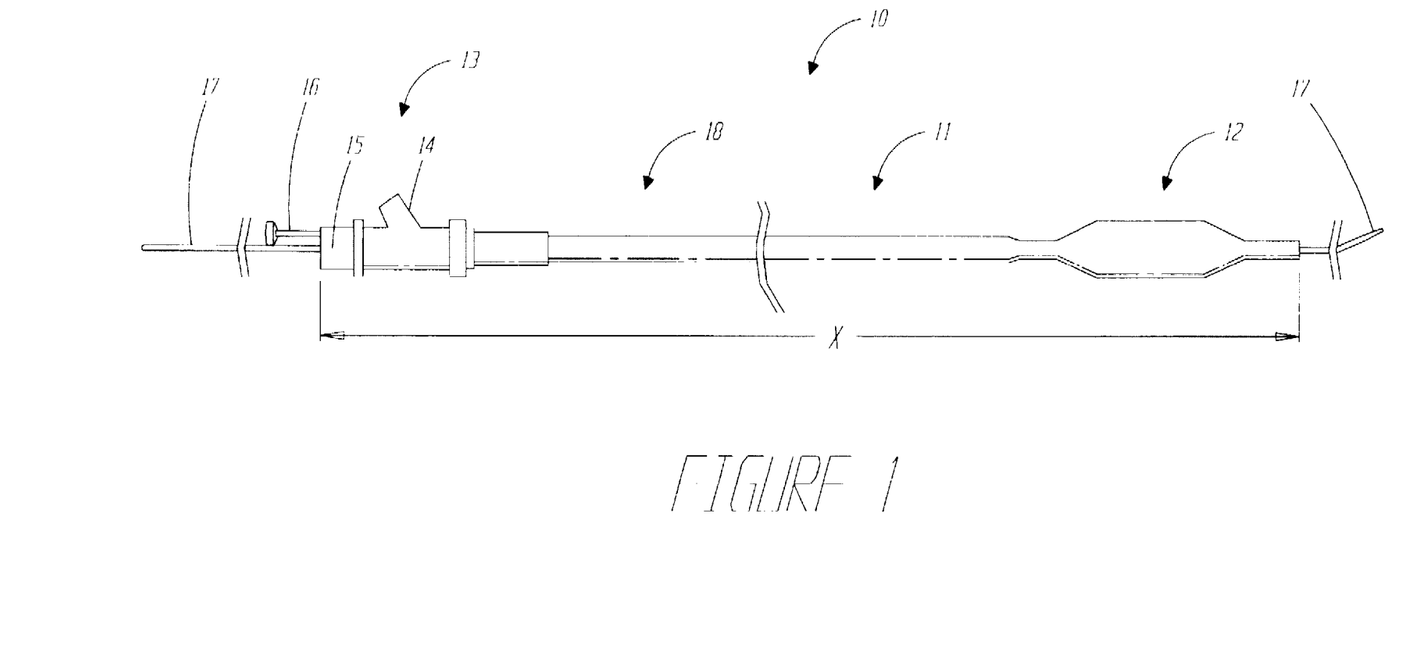
FIG. 1 is a plan view of a first embodiment of the present invention in the extended position.

FIG. 1 represents a first embodiment of the present invention in the extended position. Catheter 10 is designed to be used in combination with a removable guide wire 17. The construction and use of guide wire 17 is well known in the art and thus will not be discussed in detail herein. Dimension 'X' corresponds to the sum total of the lengths of the manifold 13, shaft 11 and balloon 12 when the catheter 10 is in the extended position. Dimension 'Z' (not shown) corresponds to the length of the guide wire 17 which remains outside the body when the catheter 10 and guide wire 17 are in use.

Figure 2:
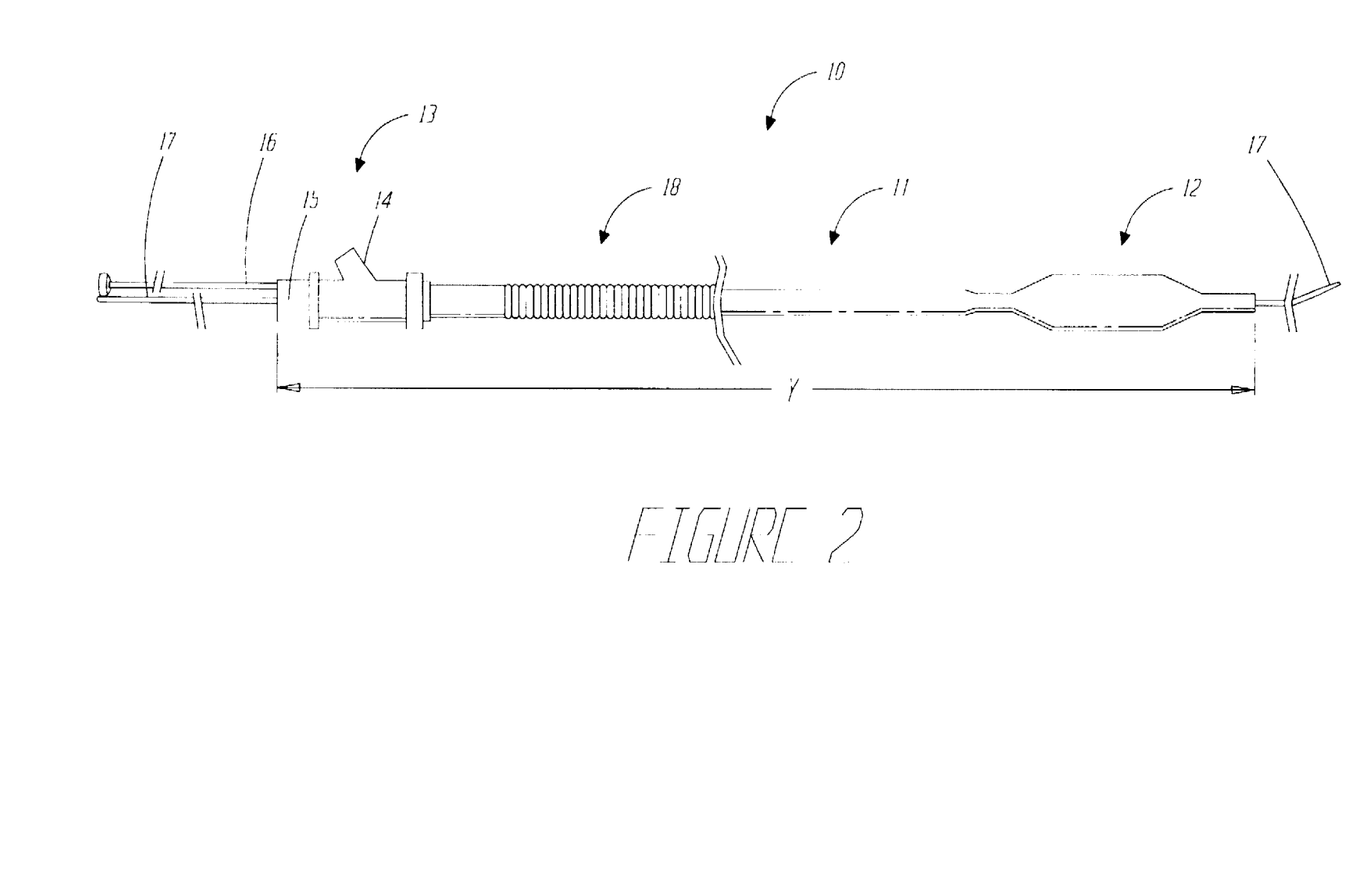
FIG. 2 is a plan view of the first embodiment in the collapsed position.

FIG. 2 represents the first embodiment of the present invention in the collapsed position. Dimension 'Y' corresponds to the sum total of the lengths of the manifold 13, shaft 11 and balloon 12 when the catheter 10 is in the collapsed position. As in FIG. 1, dimension 'Z' corresponds to the length of the guide wire 17 which remains outside the body when the catheter 10 and guide wire 17 are in use. To facilitate removing the catheter 10 while leaving the guide wire 17 in place inside the body, the extended catheter length 'X' is collapsed to dimension 'Y' such that dimension 'Y' is less than dimension 'Z'.

For example, the length of the catheter 10 in the extended position ('X') is equal to the length of a typical non-collapsible catheter. In PTCA, a common catheter length is about 135 cm, a common guide wire length is about 175 cm and both extend about 100 to 120 cm into the body. Thus, the length of the guide wire 17 extending outside the body ('Z') is between 30 and 50 cm. In order to remove the catheter 10 while the guide wire 17 remains in place, the catheter 10 must be collapsed such that the collapsed length ('Y') is less than 55 to 75 cm.

Referring to FIGS. 1 and 2, catheter 10 includes shaft 11 which in turn includes a longitudinally collapsible section 18, preferably at the proximal end of the shaft 11. A balloon 12 is operably connected to the distal end of the shaft 11 and may be formed of various materials and by various processes conventional in the art such as blow molded polyolefin copolymer. A manifold 13 is operably connected to the proximal end of the shaft 11 and may be formed of various materials and by various processes conventional in the art such as injection molded polycarbonate. The manifold 13 includes a guide wire port 15 and an inflation port 14. The guide wire 15 port may include a hemostatic seal (not shown) to lock and seal on the guide wire 17 which extends therethrough. The inflation port 14 is adapted to be connected to an inflation device such as a fluid syringe (not shown).

A rigid actuating member 16 extends through the manifold 13 and is fixed to the distal end of the collapsible section 18. The actuating member 16 is slidable relative to the manifold 13. When the actuating member 16 is pulled proximal relative to the manifold 13, the collapsible portion 18 of the shaft 11 is reduced in length a proportional amount. Since the manifold 13 locks on the guide wire 17 by use of a hemostatic seal or the like (not shown), the guide wire 17 remains in place while the catheter 10 is collapsed. Once the catheter 10 is collapsed a sufficient length ('Y'<'Z'), the guide wire 17 can be released from the manifold 13 and the catheter can be removed from the body and slid off the guide wire 17.

Figure 3:
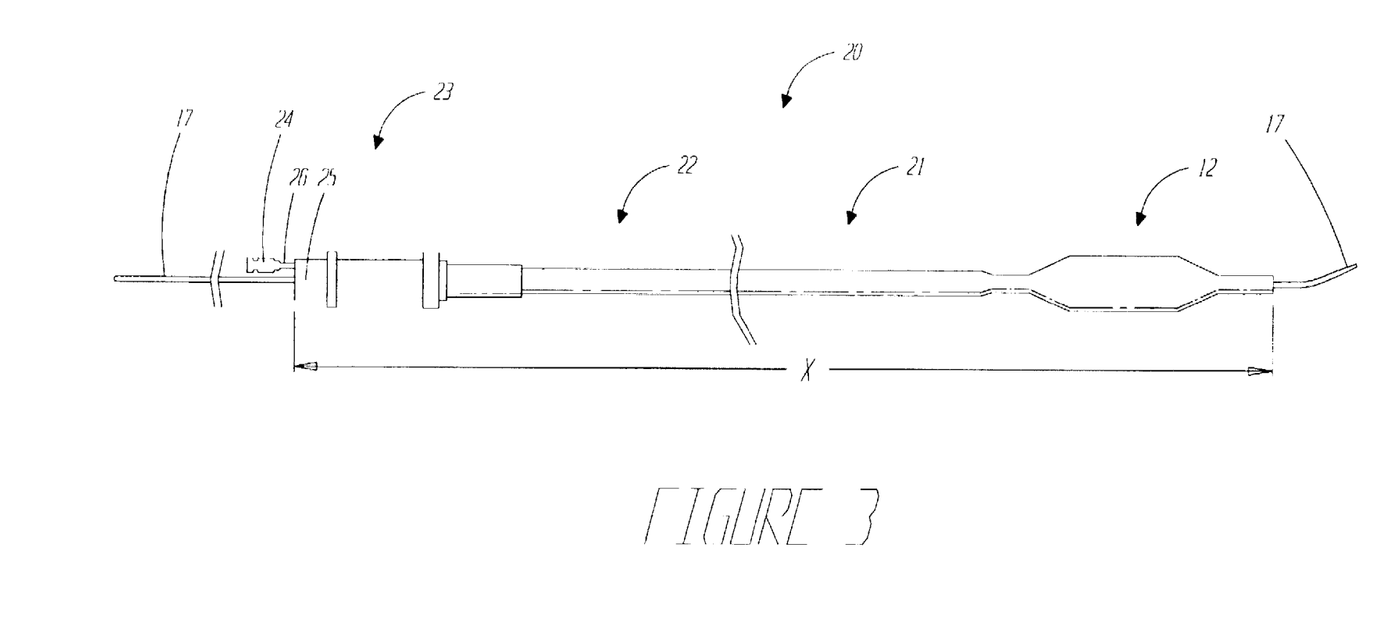
FIG. 3 is a plan view of a second embodiment of the present invention in the extended position.

Refer now to FIG. 3 which represents a second embodiment of the present invention in the extended position. Catheter 20 is designed to be used in combination with a removable guide wire 17. Dimension 'X' corresponds to the sum total of the lengths of the manifold 23, shaft 21 and balloon 12 when the catheter 20 is in the extended position. Dimension 'Z' corresponds to the length of the guide wire 17 which remains outside the body when the catheter 20 and guide wire 17 are in use.

Figure 4:
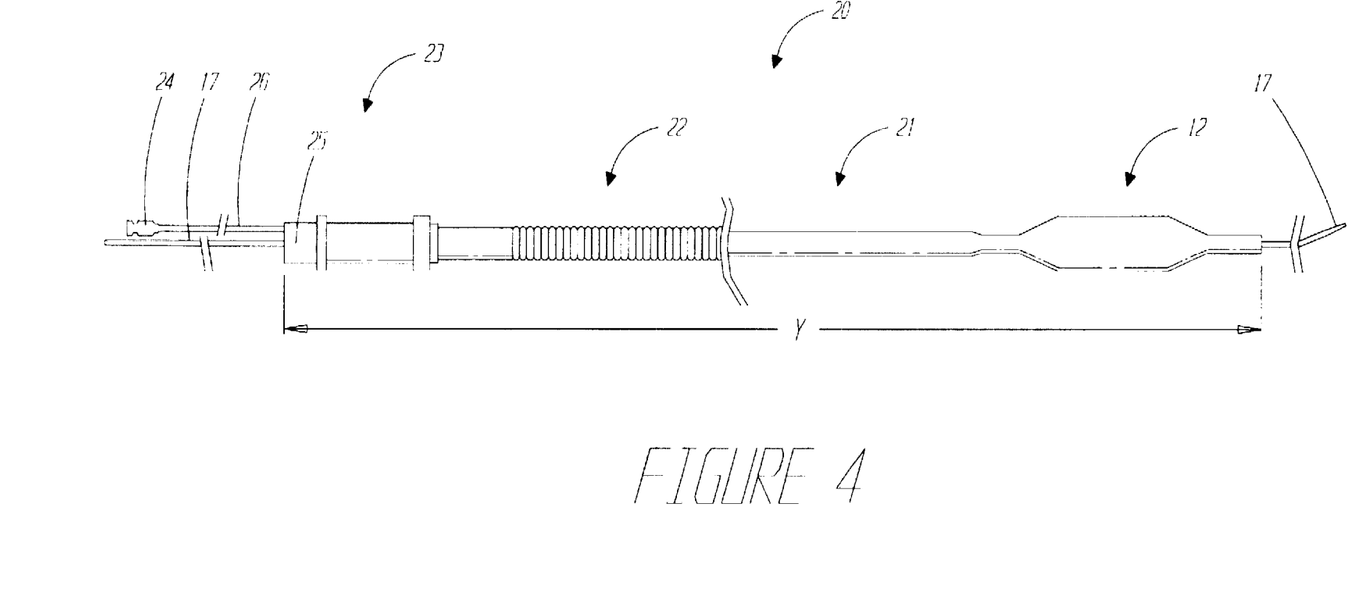
FIG. 4 is a plan view of the second embodiment in the collapsed position.

FIG. 4 represents the second embodiment of the present invention in the collapsed position. Dimension 'Y' corresponds to the sum total of the lengths of the manifold 23, shaft 21 and balloon 12 when the catheter 20 is in the collapsed position. As in FIG. 3, dimension 'Z' corresponds to the length of the guide wire 17 which remains outside the body when the catheter 20 and guide wire 17 are in use. To facilitate removing the catheter 20 while leaving the guide wire 17 in place inside the body, the extended catheter length 'X' is collapsed to dimension 'Y' such that dimension 'Y' is less than dimension 'Z'.

The second embodiment as depicted in FIGS. 3 and 4 is substantially similar to the first embodiment as depicted in FIGS. 1 and 2 with the following exceptions. Referring to FIGS. 3 and 4, manifold 23 incorporates a guide wire lumen 25, but the inflation port 24 is located on the actuating member 26. The actuating member 26 serves as an inflation tube to inflate the balloon 12 and also serves as an actuator to extend and collapse the collapsible section 22 of the shaft 21. By combining the inflation lumen into the actuating member 26, the profile of the shaft 21 can be reduced without compromising inflation/deflation time of the balloon 12. In addition, the construction of the shaft 21 and in particular the collapsible section 22 is simplified because the inflation lumen need not be designed to longitudinally collapse.

Figure 5:
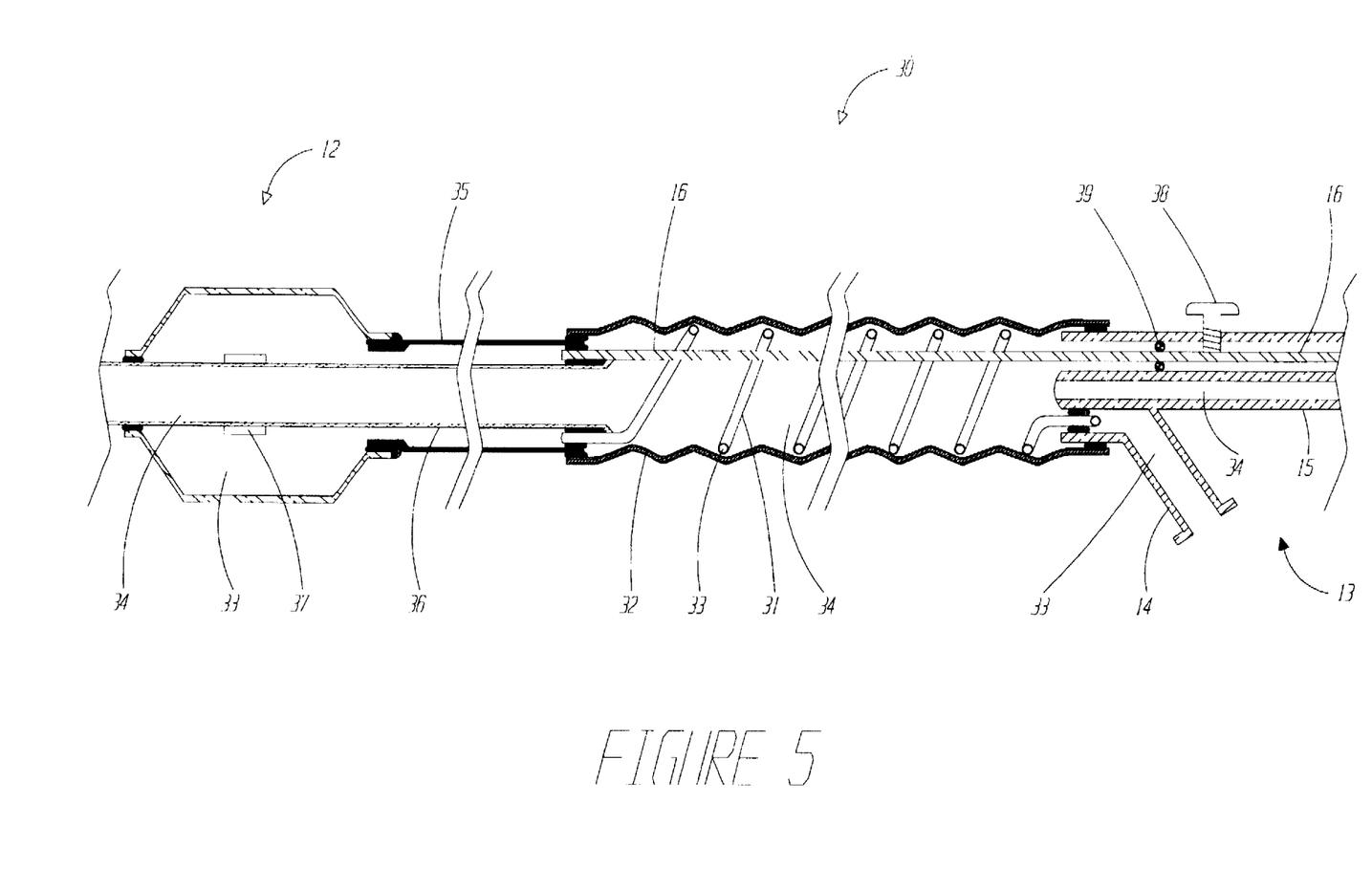
FIG. 5 is a longitudinal sectional view of a first alternative of the first embodiment.

FIG. 5 depicts a first alternative to the first embodiment shown in FIGS. 1 and 2. The catheter 30 includes a helical tube 31 surrounded by a thin polymer sheath 32 which can be longitudinally collapsed by pulling actuating member 16 in the proximal direction. The helical tube 31 defines an inflation lumen 33 extending along the helical axis and a guide wire lumen 34 extending along the longitudinal axis. The helical tube 31 is connected at its proximal end to the manifold 13 such that the inflation lumen 33 is in fluid communication with the inflation port 14. The helical tube 31 is connected at its distal end to the proximal ends of an inner tube 36 and an outer tube 35 such that the inflation lumen 33 is in fluid communication with the annular space defined between the outer tube 35 and the inner tube 36. The distal end of the outer tube 35 is connected to the proximal end of the balloon 12 and the distal end of the inner tube 36 is connected to the distal end of the balloon 12. A radiopaque marker band 37 is placed at a mid point inside the balloon 12 preferably on the inner tube 36. The actuating member 16 extends through the manifold 13, through the guide wire lumen 34 defined by the helical tube 31 and is indirectly connected to the distal end of the helical tube 31 preferably adjacent the connection to the inner tube 36 and the outer tube 35. A lock screw 38 may be incorporated into the manifold 13 in order to fix the longitudinal position of the actuating member 16. In addition, an o-ring 39 may be incorporated into the manifold 13 to seal about the actuating member 16 in order to prevent blood from entering the guide wire lumen 34 and to infuse fluids distally through the guide wire lumen 34.

The manifold 13 is preferably formed of polycarbonate by a process of injection molding. The o-ring is preferably made of a relatively soft durometer material such as rubber or elastomer. The lock screw 38 is preferably formed of polycarbonate by a process of injection molding. Alternatively, the lock screw 38 may be formed of medical grade stainless steel. The materials and manufacturing processes for the manifold 13, the lock screw 38 and the o-ring 39 are conventional in the art and those skilled in the art will recognize alternate materials and manufacturing processes may be employed.

As an alternative to the lock screw 38, a cam type lock mechanism (not shown) may be used. With this type of mechanism, the lock may be toggled between (1) locking on the guide wire 17 with the actuating member 16 free to move and (2) locking on the actuating member 16 with the guide wire 17 free to move. This construction simplifies the method of using the device.

The helical tube 31 is preferably formed of a polyolefin copolymer by a series of processes including in sequence, extrusion, irradiation, and pressurized thermal forming. In addition, a support member may extend with the helical tube 33 such as a fiber reinforcement or coil made of stainless steel, super elastic alloy or a polymer. The purpose of this processing is to construct a flexible, thin walled, high pressure tube capable of navigating though tortuous anatomy, longitudinally collapsing to a compact size and inflating to pressures in excess of 15 atm. The polymer sheath 32 can be formed of any medical grade polymer which is thin walled, flexible, preferably lubricious and durable. For example, the sheath 32 can be formed of a heat shrunk polyolefin copolymer. Other materials and processing will satisfy these functional criteria.

The actuating member 16 is preferably formed of a super elastic alloy or stainless steel. Rigid polymers or composites may also be used and the actuating member 16 may either be a solid rod or a hollow tube to transport fluids. In addition, the actuating member 16 may be tapered along its length to impart varying flexibility. Those skilled in the art will recognize other suitable materials and constructions may be employed to serve substantially the same function.

The outer and inner tubes 35, 36 are preferably formed of extruded polyethylene tubes aligned coaxially. The inner and outer tubes 35, 36 may also be formed integrally as in a dual lumen extrusion. The balloon 12 is preferably formed of an extruded, irradiated and blow molded polyolefin copolymer. The balloon 12 may also be formed integrally with the outer tube 35. The outer and inner tubes 35,36 and the balloon 12 may also be formed of nylon, polyethylene, polyethylene terephthalate and other materials conventional in the art.

Connections between components are preferably made using adhesives such as cyanoacrylate and other suitable adhesives well known in the art. Connections between polymer components can also be made using other bonding techniques such as thermal welding, ultrasonic welding and the like.

Figure 6:
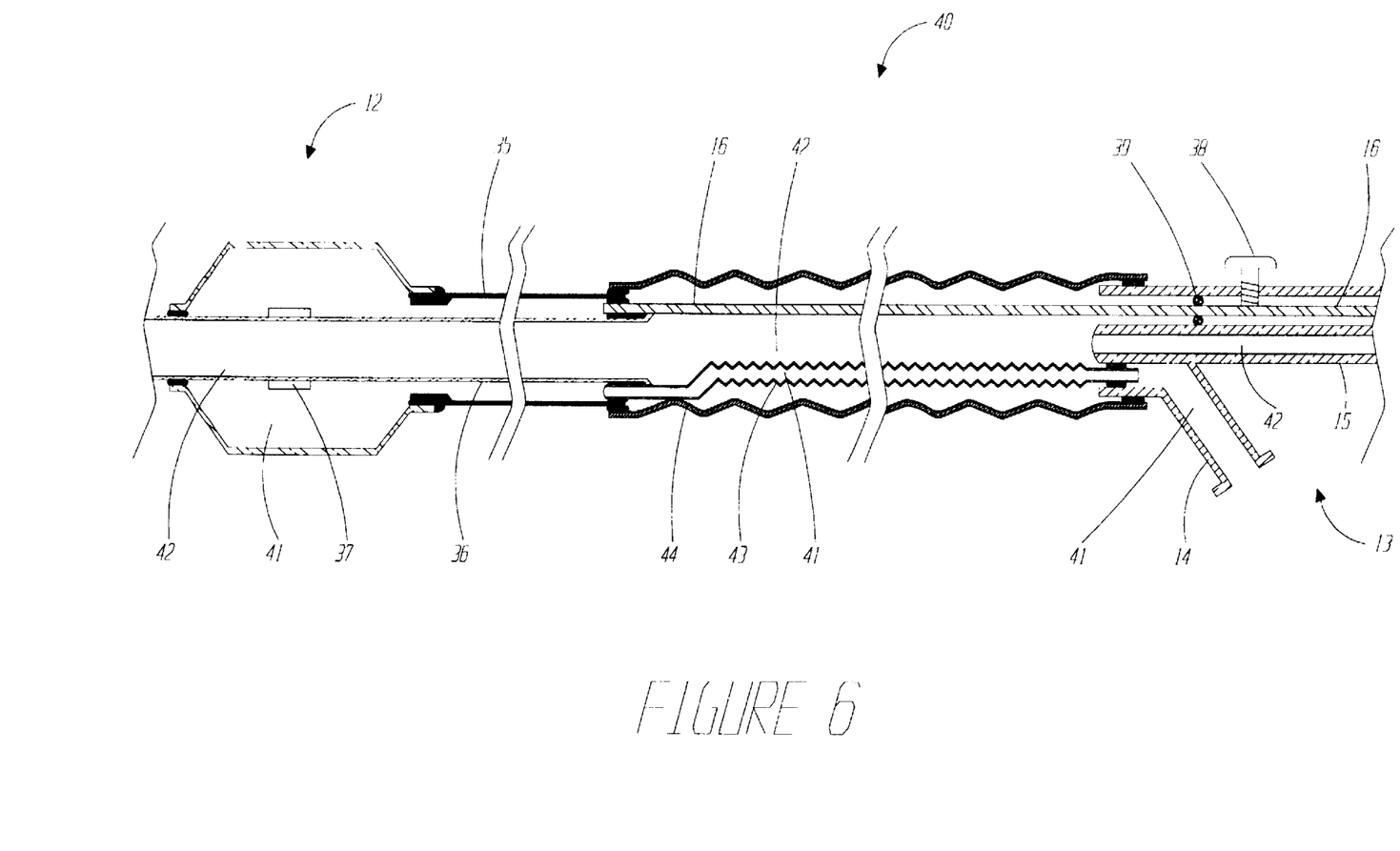
FIG. 6 is a longitudinal sectional view of a second alternative of the first embodiment.

Refer now to FIG. 6 which shows a second alternative to the first embodiment as shown in FIGS. 1 and 2. The catheter 40 is similar to catheter 30 in FIG. 5 with the following differences. The catheter 40 includes a longitudinally collapsible inflation bellow 43 defining an inflation lumen 41, and a longitudinally collapsible outer bellow 44 defining a guide wire lumen 42. The inflation bellow 43 is preferably disposed within the outer bellow 44 but the inflation bellow 43 may also be located exterior to the outer bellow 44. In addition, the inflation bellow 43 and the outer bellow 44 may be formed integrally as in a dual lumen extrusion. The tendency to collapse longitudinally may be imparted by forming flex points along the length of the bellows 43, 44. The flex points can be formed by a series of recesses or a series of folds. Alternatively, the bellows 43, 44 may be formed by heat shrinking a polymer over a coil, substantially similar to flexible venting used for household appliances (vacuum, clothes dryer, etc.) and automobiles but on a reduced scale. Those skilled in the art will recognize that other materials and constructions not mentioned above will serve substantially the same function.

A third alternative (not shown) to the first embodiment contemplates switching the function of the lumens defined by the outer bellow 44 and the inflation bellow 43. More specifically, the inflation bellow 43 is connected at its proximal end to the guide wire port 15 and connected at its distal end to the proximal end of the inner tube 36. With this arrangement, the inflation bellow 43 now defines a guide wire lumen and the annular space between the inflation bellow 43 and the outer bellow 44 defines the inflation lumen.

Figure 7:
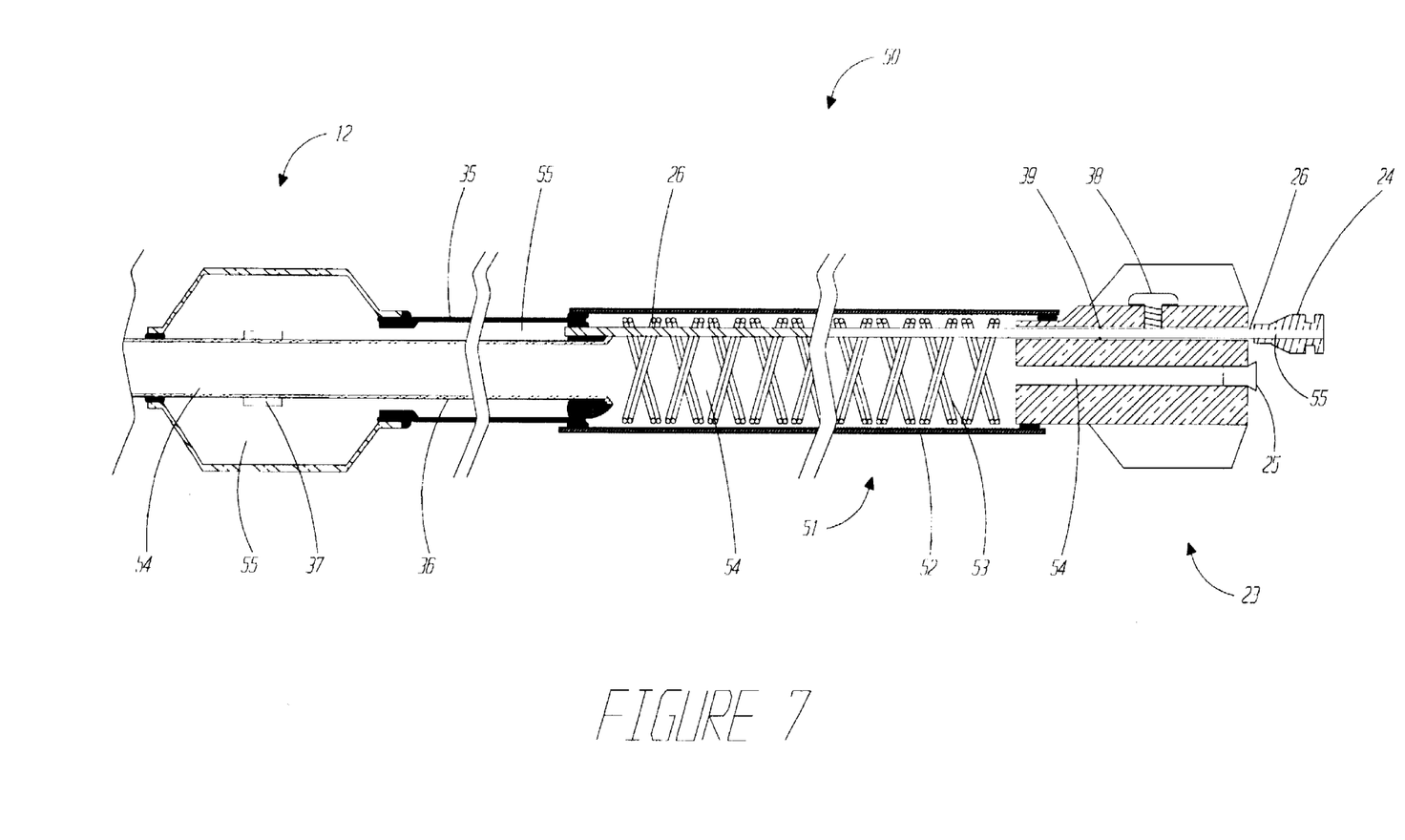
FIG. 7 is a longitudinal sectional view of a first alternative of the second embodiment.

Refer now to FIG. 7 which shows a first alternative to the second embodiment as shown in FIGS. 3 and 4. The catheter 50 is similar to catheter 30 shown in FIG. 5 with the following exceptions. The catheter 50 includes an actuating member 26 which defines an inflation lumen 55 therethrough, and a longitudinally collapsible polymer encased braid 51 which defines a guide wire lumen 54 therethrough. The actuating member 26 is preferably disposed within the polymer encased braid 51 but the actuating member 26 may also be located exterior to the polymer encased braid 51. As differentiated from the first embodiment, catheter 50 combines the features of the actuating member 26 with the inflation lumen 55 into a single component.

The actuating member 26 is preferably formed of a super elastic alloy or stainless steel. Rigid tubular polymers or composites may be used in place of the metal. In addition, the actuating member 26 may be tapered along its length to impart varying flexibility. The manifold 23 and inflation port 24 are formed in a similar manner as manifold 13.

The polymer encased braid 51 includes a polymer encasement 52 and a braid 53. The polymer encasement 52 is preferably formed of a urethane coating but may be formed of any thin walled polymer coating or tube capable of efficient longitudinal collapse. The braid 53 is preferably formed of super elastic alloy wires approximately 0.001 to 0.003 inches in diameter. A coil or mesh may be used in place of the braid 53, and other suitable materials such as stainless steel, polymer fibers and the like may be employed as well.

It should be noted that the different constructions of longitudinally collapsible tubes described herein are interchangeable. For example, the polymer encased braid 51 in FIG. 7 may be replaced with a bellow 44 in FIG. 6, and visa-versa. The key features of the longitudinally collapsible tubes include, without limitation: low profile both proximally and distally when extended, relatively thin walls for low profile and large interior lumens, efficient packing upon collapse, able to sustain high inflation pressures, flexible, pushable and trackable. As such, those skilled in the art will recognize alternate materials, methods of manufacture and constructions not disclosed herein are suitable for the intended function.

In practice, the catheter of the present invention is used in combination with a removable guide wire which can be inserted into the patient before or simultaneously with the catheter. The technique of inserting the guide wire before the catheter is commonly referred to as "bare wire" or "wire first". The "wire first" technique is almost exclusively practiced with RX type catheters. Inserting the guide wire and the catheter simultaneously is a technique almost exclusively practiced with OTW type catheters. The catheter of the present invention allows for both techniques to be utilized.

As an example, a medical procedure utilizing the present invention may follow these steps: (1) a guide wire is inserted into a patient such that the guide wire extends from a point outside the patient to a point inside the patient; (2) a balloon catheter is positioned over the guide wire such that the entire length of the balloon catheter is on the guide wire (step 2 may be performed before or after step 1); (3) the balloon catheter is compressed longitudinally such that the length of the balloon catheter is shorter than the length of the guide wire outside the patient, and; (4) the balloon catheter is removed from the guide wire. These steps may be performed in sequence listed or in a different sequence depending on the nature and needs of the therapy provided to the patient.

As another example, a medical procedure utilizing the present invention may follow the following steps: (1) a guide wire is inserted into a patient such that the guide wire extends from a point outside the patient to a point inside the patient; (2) the balloon catheter is compressed longitudinally such that the length of the balloon catheter is shorter than the length of the guide wire outside the patient (the catheter may be locked in the compressed position); (3) the balloon catheter is positioned over the guide wire such that the entire length of the balloon catheter is on the guide wire (the guide wire may be locked in place); (4) the balloon catheter is extended such that the balloon catheter extends to the point inside the patient (the catheter may be locked in the extended position); (5) therapy is provided to the patient using the balloon catheter; (6) the balloon catheter is compressed longitudinally such that the length of the balloon catheter is shorter than the length of the guide wire outside the body, and; (7) the balloon catheter is removed from the guide wire. Again, the steps may be performed in the sequence listed or in a different sequence depending on the nature and needs of the therapy provided to the patient. It is noted that the methods described above are not necessarily limited to balloon catheters, as other catheter types may reap similar benefits in use and construction.

As a further example, the present invention may be used to exchange a guide wire while leaving the catheter in place inside the patient, and retaining the ability to facilitate a catheter exchange without the use of an extension wire. Thus, in practice, a medical procedure utilizing the present invention may follow the following steps: (1) a guide wire is inserted into a patient such that the guide wire extends from a point outside the patient to a point inside the patient; (2) either before or after the guide wire is placed inside the patient, a balloon catheter is positioned over the guide wire such that the entire length of the balloon catheter is on the guide wire; (3) if it becomes necessary to remove the guide wire, it is simply pulled out while the catheter remains inside the body; (4) the treating physician then inserts a new guide wire and continues with the procedure.

While the specification describes the preferred constructions, methods and materials of manufacture and methods of practice, those skilled in the art will appreciate the scope and spirit of the invention with reference to the appended claims.

What is claimed is:

1. A method of removing a balloon catheter over a guide wire, comprising the steps of:
   (a) inserting a guide wire into a patient such that the guide wire extends from a point outside the patient to a point inside the patient;
   (b) positioning a balloon catheter over the guide wire such that the entire length of the balloon catheter is on the guide wire;
   (c) compressing the balloon catheter longitudinally such that the entire length of the balloon catheter is shorter than the length of the guide wire outside the patient; and
   (d) removing the balloon catheter from the guide wire.

2. A method of removing a balloon catheter over a guide wire, comprising the steps of:
   (a) inserting a guide wire into a patient such that the guide wire extends from a point outside the patient to a point inside the patient;
   (b) compressing a balloon catheter longitudinally such that the entire length of the balloon catheter is shorter than the length of the guide wire outside the patient;

(c) positioning the balloon catheter over the guide wire such that the entire length of the balloon catheter is on the guide wire;

(d) extending the balloon catheter such that the balloon catheter extends to the point inside the patient;

(e) providing therapy to the patient using the balloon catheter;

(f) compressing the balloon catheter longitudinally such that the entire length of the balloon catheter is shorter than the length of the guide wire outside the body; and (g) removing the balloon catheter from the guide wire.

3. A method of removing a balloon catheter over a guide wire as in claim 1 or 2, wherein the balloon catheter is positioned on the guide wire prior to inserting the guide wire into the patient.

4. A method of removing a balloon catheter over a guide wire as in claim 1 or 2, wherein the balloon catheter is positioned on the guide wire subsequent to inserting the guide wire into the patient.

5. A method of removing a balloon catheter over a guide wire as in claim 1 or 2, wherein the guide wire is releasably locked relative to a proximal end of the balloon catheter.

6. A method of removing a balloon catheter over a guide wire as in claim 1 or 2, further comprising a lock element connected to the proximal end of the catheter which releasably fixes the length of the catheter.

* * * * *

UNITED STATES PATENT AND TRADEMARK OFFICE
CERTIFICATE OF CORRECTION

PATENT NO. : 5,779,671

DATED : July 14, 1998

INVENTOR(S) : RESSEMANN et al.

It is certified that error appears in the above-identified patent and that said Letters Patent is hereby corrected as shown below:

On title page, in [56] References Cited, U.S. Patent Documents, insert:

--4,479,497    10/1984    Fogarty et al.

4,564,014    1/1986    Fogarty et al.

4,652,259    3/1987    O'Neil--

Signed and Sealed this

First Day of December, 1998

*Attest:*

BRUCE LEHMAN

*Attesting Officer*    *Commissioner of Patents and Trademarks*